United States Patent [19]

Maurice

[11] Patent Number: 4,623,337
[45] Date of Patent: Nov. 18, 1986

[54] LIQUID DISPENSING APPARATUS

[75] Inventor: David M. Maurice, Atherton, Calif.

[73] Assignee: Alpha Group, Inc., Laguna Beach, Calif.

[21] Appl. No.: 587,663

[22] Filed: Mar. 8, 1984

[51] Int. Cl.[4] .......................................... A61M 35/00
[52] U.S. Cl. .................................... 604/298; 222/390
[58] Field of Search ............... 604/209, 211, 224, 218, 604/294, 295, 298, 300–302; 222/333, 340, 390, 360

[56] References Cited

U.S. PATENT DOCUMENTS

| | | | |
|---|---|---|---|
| 3,162,217 | 12/1964 | Poli, Jr. et al. | 604/211 |
| 4,013,370 | 3/1977 | Gingras | 222/309 |
| 4,498,904 | 2/1985 | Turner et al. | 604/224 |
| 4,531,944 | 7/1985 | Bechtle | 604/302 |

Primary Examiner—John D. Yasko
Assistant Examiner—J. L. Kruter
Attorney, Agent, or Firm—Willis E. Higgins; Edward B. Gregg

[57] ABSTRACT

An apparatus (10) for the repetitive dispensing of a predetermined quantity of eyedrops (12) has a cylinder (14) with a restricted opening (18) at a first end (16). A plunger (20) attached to rod (23) extends into the cylinder (14) from end (22). Biasing member (28) has a ramped cam surface (32) incorporating a pair of steps (46), actuating member (26) has an opposed surface (30) with a projection (44) which rides on ramped cam surface (32) and drops off step (46) when actuating member (26) is rotated. Rotation of the actuating member (26) also advances the actuating member (26) on threaded member (24). Spring (42) biases surfaces (30) and (32) together. A projection (44) drops over each step (46), plunger (20) is moved incrementally toward end (16) of cylinder (14) to discharge eyedrops (12) through opening (18). A disposable cartridge (50) may be substituted for the cylinder (14).

15 Claims, 9 Drawing Figures

LIQUID DISPENSING APPARATUS

BACKGROUND OF THE INVENTION

1. Field of the Invention

This invention relates to an apparatus for the repetitive dispensing of a predetermined quantity of a liquid. It also relates to a cartridge containing the liquid to be dispensed in the apparatus. Most especially, it relates to such an apparatus and cartridge which are especially adapted for dispensing eyedrops in an improved manner.

2. Description of the Prior Art

Apparatus for the repetitive dispensing of a predetermined quantity of a liquid, such as eyedrops, is known in the art. For example, such an apparatus is described in my prior U.S. Pat. No. 3,934,585, issued Jan. 27, 1976. While the apparatus there disclosed performs its intended function very effectively, it is sufficiently complex in construction that it is not feasible to supply the apparatus as a disposable unit, and the user must load the apparatus from a separate supply of eyedrops. A variety of other apparatuses for dispensing eyedrops or other liquids are also known in the prior art, as disclosed in, for example, the following issued U.S. patents: Lerner et al., U.S. Pat. No. 2,920,624, issued Jan. 12, 1960; Schwartzman, U.S. Pat. No. 3,091,374, issued May 28, 1963; Petterson, U.S. Pat. No. 4,002,168, issued Jan. 11, 1977; Sbarra et al., U.S. Pat. No. 4,111,200, issued Sept. 5, 1978; and Shaw, U.S. Pat. No. 4,259,953, issued Apr. 7, 1981. However, none of these prior art patents discloses structures suitable for modifying apparatus of the general type covered by my prior issued patent so that such apparatus may be provided as a disposable unit, or alternatively, so that a portion of the apparatus may be provided as a disposable cartridge.

SUMMARY OF THE INVENTION

Accordingly, it is an object of this invention to provide an apparatus for the repetitive dispensing of a predetermined quantity of a liquid by application of pressure which is of sufficiently simplified construction that the apparatus may be provided in disposable form.

It is another object of the invention to provide an apparatus for application of eyedrops incorporating an improved, rotatable camming mechanism for actuation.

It is a further object of the invention to provide an improved, rotatable camming mechanism for actuating an apparatus for repetitive dispensing of a predetermined quantity of a liquid.

It is still another object of the invention to provide an improved cartridge containing the liquid to be dispensed in such an apparatus.

It is yet another object of the invention to provide an apparatus for the repetitive dispensing of a predetermined quantity of a liquid supplied by a bottle inserted in the apparatus, which apparatus incorporates an improved manner of equalizing pressure inside and outside the bottle.

The attainment of these and related objects may be achieved through the novel apparatus for the repetitive dispensing of a predetermined quantity of a liquid and cartridge for such an apparatus herein disclosed. An apparatus in accordance with this invention includes a cylinder having a first end and a second closed end. The first end of the cylinder has a restricted opening through which the liquid may pass in response to pressure applied to the liquid. At least one of the first and second ends is movable within the cylinder toward the other end to change volume of a space defined by the cylinder and containing the liquid. A biasing member engages the second end for moving the ends in steps toward one another. An actuating member engages the biasing member by means of opposed surfaces on each member. One of the opposing surfaces constitutes a ramped cam having at least one step. The other of the opposing surfaces has at least one projection engaging the ramped cam opposing surface. A means, such as a spring, biases the opposed surfaces toward one another. The biasing and actuating members are rotatable with respect to each other. Rotation of the biasing and actuating members with respect to each other moves the projection on the ramped cam opposing surface. Movement of the projection over the step advances the ends toward one another a distance corresponding to the step. A cartridge in accordance with the invention for insertion in an apparatus in accordance with the invention is formed from a cylinder having a first end through which the liquid is dispensed and a second, closed end. At least one of the first and second ends is movable within the cylinder toward the other end to change volume of a space defined by the cylinder toward the other end to change volume of a space defined by the cylinder between the first and second ends. The liquid to be dispensed by the apparatus fills the space in the cylinder between the two ends. In another aspect of the invention, an apparatus for the repetitive dispensing of a predetermined quantity of a liquid has a housing including a cylinder having a first end through which the liquid is dispensed through application of pressure. An opening in the housing is configured to receive a neck of a bottle. There is a reservoir in the housing connected to the opening and to the cylinder. A means in the housing applies pressure to liquid in the cylinder. A tube extends from the opening and has a length such that a first end extends above the liquid in the bottle when the bottle is in the opening. The tube has a second end connected to ambient pressure.

The simplified construction of the apparatus of this invention allows the apparatus to be provided as a disposable unit containing eyedrops or other liquid to be repetitively dispensed in predetermined quantities by the application of pressure. Alternatively, the liquid may be provided in the cartridge of this invention, for easy insertion in the apparatus. The form of the invention for use with a bottle provides improved pressure relief for the bottle.

The attainment of the foregoing and related objects, advantages and features of the invention should be more readily apparent to those skilled in the art, after review of the following more detailed description of the invention, taken together with the drawings, in which:

DETAILED DESCRIPTION OF THE INVENTION

Figure 1:
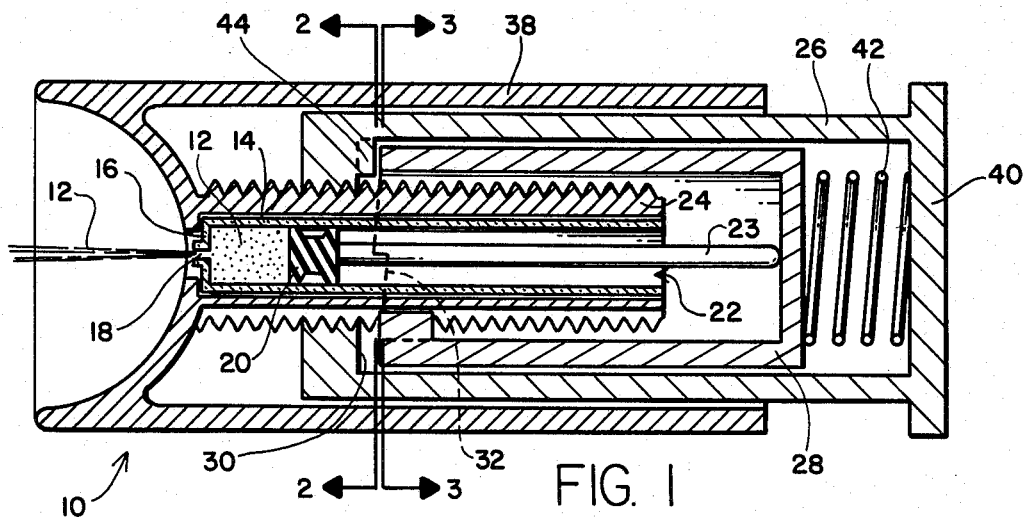
FIG. 1 is a lateral cross section view of an apparatus in accordance with the invention.
Figure 2:
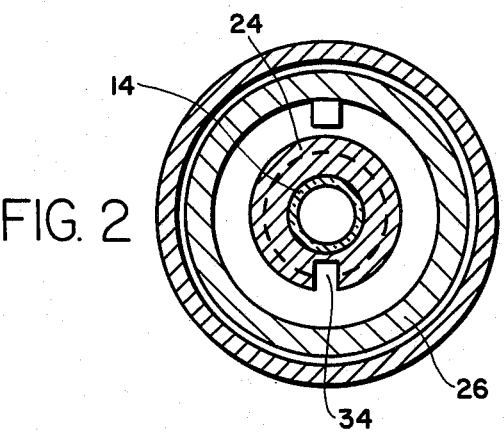
FIG. 2 is a cross section view, taken along the line 2—2 in FIG. 1.

Turning now to the drawings, more particularly to FIG. 1, there is shown an apparatus 10 for the repetitive dispensing of a predetermined quantity of eyedrops 12 through the application of pressure, in accordance with the invention. The apparatus 10 includes a cylinder 14, containing the eyedrops 12. The cylinder 14 has a first end 16 with a nozzle 18 through which the eyedrops 12 are projected. A plunger 20 extends into the cylinder 14 from a second end 22. Rod 23 extends from plunger 20 from the second end 22 of the cylinder 14. As shown, the cylinder 14 is implemented as a sleeve, which is friction fit into threaded member 24. Actuating member 26 is circumferentially disposed around the threaded member 24 and threaded thereto. A biasing member 28 is also circumferentially disposed around the threaded member 24, between the threaded member 24 and the actuating member 26. Biasing member 28 engages the rod 23. Surfaces 30 and 32, respectively on the actuating member 26 and the biasing member 28, are in opposing relationship (see also FIG. 4). Threaded member 24 has a slot 34 (FIGS. 2 and 3) extending along its length. Biasing member 28 has a spline 36 (FIG. 3), which fits into the slot 34 to prevent rotation of the biasing member 28 with respect to the threaded member 24. Threaded member 24 forms part of housing 38, which extends around the apparatus, with the exception of handle 40. A compressed spring 42 is connected to handle 40 and extends between the handle 40 of actuating member 26 and the biasing member 28.

Figure 3:
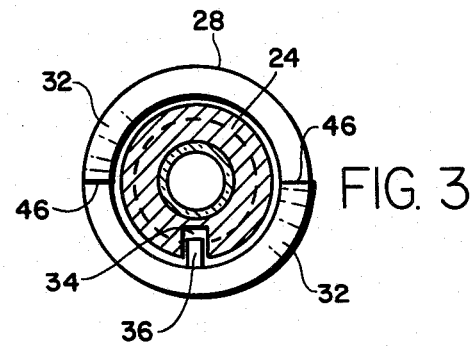
FIG. 3 is a cross section view, taken along the line 3—3 in FIG. 1.
Figure 4:
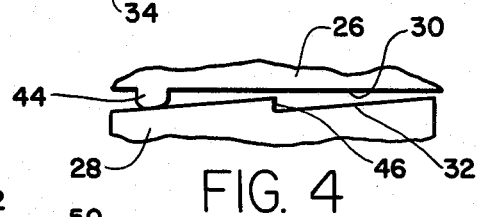
FIG. 4 is an enlarged view of a portion of the apparatus shown in FIG. 1.

Details of a ramped cam mechanism formed by surface 32 on biasing member 28 and projection 44, extending from surface 30 on actuating member 26 are shown in FIGS. 3 and 4. There is a pair of steps 46 on the surface 32. The surface 32 is inclined, leading up to each step 46. Spring 42 (FIG. 1) biases the surfaces 30 and 32 toward one another. Projection 44 rides up the inclined surface 32 to each step 46 as knob 40 is turned. Turning the knob 40 also advances the actuating member 26 on the threaded member 24 toward first end 16 of the cylinder 14. When the projection 44 drops over step 46, biasing member 28 is also permitted to move in stepwise increments corresponding to the height of step 46 toward first end 16 of the cylinder 14. Biasing member 28 then pushes against rod 23, to push the plunger 20 toward first end 16 of the cylinder 14 a corresponding amount. The resulting pressure on eyedrops 12 discharges a predetermined amount of the eyedrops 12 through the nozzle 18 in the form of a jet. For each half revolution of the actuating member 26, the stepwise movement of plunger is repeated, until the plunger 20 has reached end 16 of the cylinder 14. The pitch of the threads on threaded member 24 and actuating member 26 should be dimensioned so that leftward motion of the actuating member 26 for each half revolution on threaded member 24 corresponds to the height of step 46. The eyedrops 12 should completely fill the space between end 16 and plunger 20 at all times. Trapped air in this space would produce unpredictable operation due to compression of the air. Because the ramped cam mechanism is not visible in operation of the dispenser, the user does not know when the jet of eyedrops will be discharged, and so does not blink in anticipation.

Figure 5:
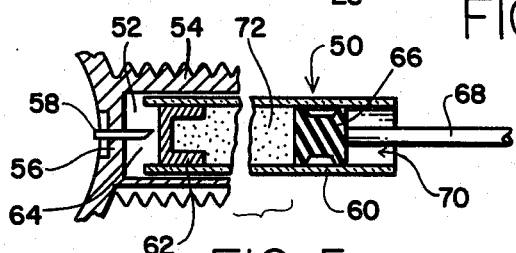
FIG. 5 is a cross section view of a portion of another apparatus in accordance with the invention.
Figure 6:
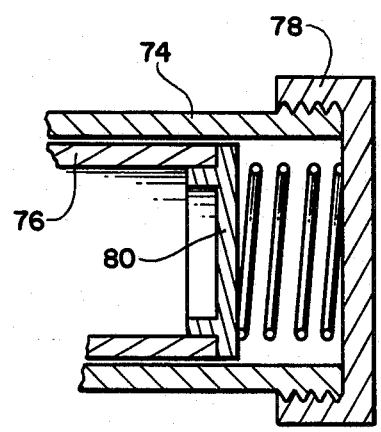
FIG. 6 is another cross section view of another portion of the apparatus in FIG. 5.

FIGS. 5 and 6 show portions of another embodiment of an apparatus in accordance with the invention, in which the cylinder 14 is replaced with an insertable cartridge 50, which is slidably positioned in bore 52 of a threaded member 54, corresponding to the threaded member 24 in FIG. 1. Bore 52 has a wall 56 through which a hollow needle 58 extends. Cartridge 50 has a cylinder 60, formed from glass or a rigid plastic. End plug 62, formed from a resilient, puncturable plastic is inserted in end 64 of the cylinder 60. A plunger 66 and rod 68 are inserted in the other end 70 of the cylinder 60, with the eyedrops 72 between the plug 62 and the plunger 60. Actuating member 74 and biasing member 76 respectively correspond to the actuating member 26 and biasing member 28 in FIG. 1. The actuating member 74 and biasing member 76 each have removable caps 78 and 80 to allow insertion and removal of new and spent cartridges 50. In other respects, the construction and operation of the FIGS. 5 and 6 embodiment of the invention is the same as the FIGS. 1 through 4 embodiment.

Figure 7:
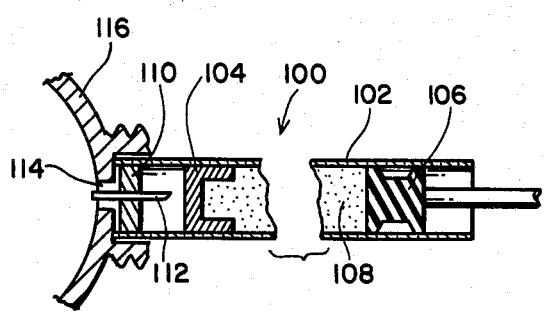
FIG. 7 is another cross section view of a portion of another apparatus in accordance with the invention.

FIG. 7 shows another form of an insertable cartridge 100 for use in a dispensing apparatus in accordance with the invention. As in the FIG. 5 embodiment, the cartridge 100 has a cylinder 102, formed from glass or a rigid plastic, a plug 104 near one end of the cylinder 102, and a plunger 106 extending into the cylinder 102 from the other direction. Liquid 108 to be dispensed fills the space between plug 104 and plunger 106. A second plug 110 is mounted in the tube 102 on the other side of plug 104 from the liquid 108. Plug 110 supports an axially disposed, hollow needle 112, positioned to puncture the resilient plug 104 in a manner similar to that of the needle 58 in FIG. 5. Needle 112 extends through aperture 114 in eyecup 116. In other respects, the construction and operation of the FIG. 7 embodiment of the invention is the same as the FIGS. 1 through 4 embodiment.

Figure 8:
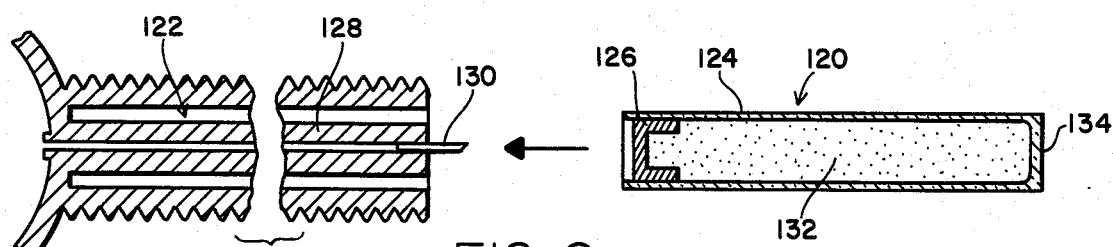
FIG. 8 is another cross section view of a portion of yet another apparatus in accordance with the invention.

FIG. 8 shows another form of a cartridge 120 and puncturing assembly 122 for use with the cartridge 120. The cartridge 120 has a cylinder 124, closed at one end and having a plug 126 near the other end, similar to the plugs 62 and 104 in FIGS. 5 and 7. The puncturing assembly 122 has a cylindrical mandrel 128 having an axially disposed puncturing needle 130 positioned to puncture resilient end plug 126 of the cartridge 120. Liquid 132 fills the space defined by cylinder 124 and plug 126. Cylinder 124 is dimensioned so that mandrel 128 enters the cylinder 124 as the cartridge 120 is pushed to the left during operation of the apparatus. Since the cartridge 120 does not employ a plunger and rod, a biasing member corresponding to biasing member 28 in FIG. 1 presses directly against end 134 of the cartridge 120. In other respects, the construction and operation of a dispensing apparatus incorporating the cartridge 120 and puncturing assembly 122 in FIG. 8 is the same as the FIGS. 1 through 7 embodiments.

Figure 9:
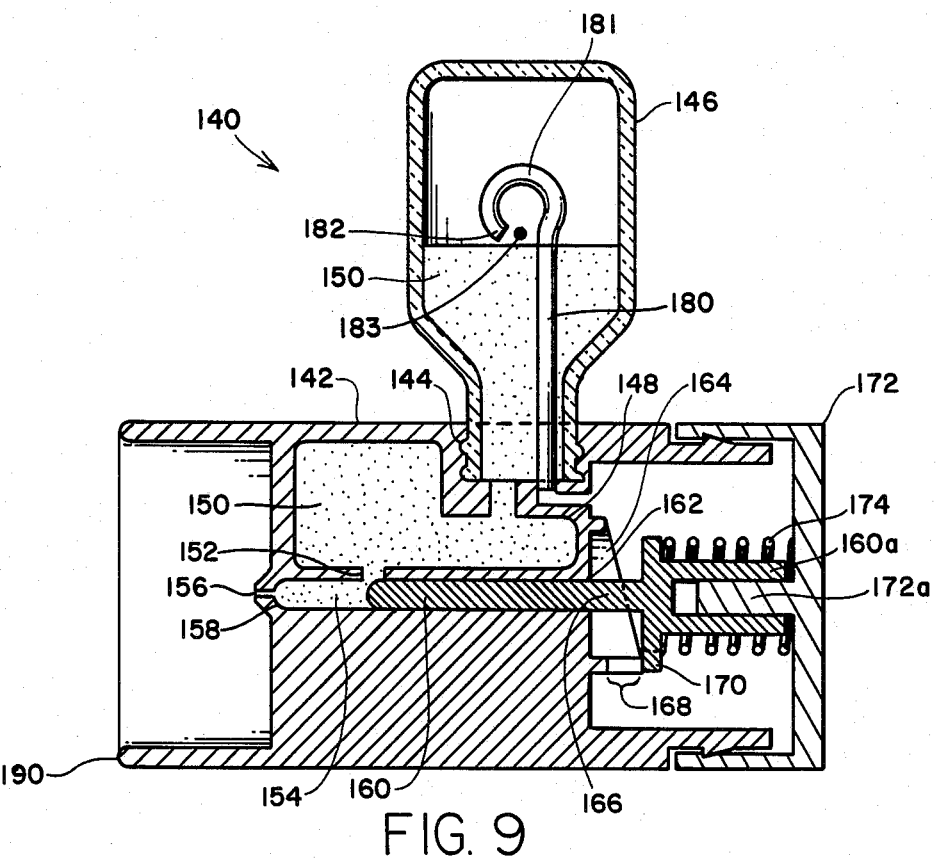
FIG. 9 is a cross section view of still another apparatus in accordance with the invention.

FIG. 9 shows another dispensing apparatus 140 in accordance with the invention. The apparatus 140 has a generally cylindrical shaped body 142 having a threaded opening 144 into which a conventional eyedrop bottle 146 is inserted as shown. The body 142 contains a reservoir 148, into which eyedrops 150 flow from the bottle 146. Conduit 152 connects the reservoir 148 to cylinder 154. The cylinder 154 has a restricted opening 156 at end 158 and a plunger 160, extending into the cylinder 154 from end 162. A ramped cam 164 is disposed circumferentially around end 166 of the plunger 160, extending from the end 162 of cylinder 154. Ramped cam 164 has a step 168, which defines a path of travel of the plunger 160 within cylinder 154. Projection 170 on the plunger 160 rides on the ramped cam 164 and drops over step 168 to define the stroke of plunger 160 within cylinder 154. Knob 172 is turned to move the projection 170 along ramped cam 164. Spring 174 connects plunger 160 and knob 172, and is compressed to urge the plunger 160 toward end 158 of the cylinder 154. Rectangular portion 172a of knob 172 extends into portion 160a of plunger 160 so that rotary motion of knob 172 is transmitted to plunger 160.

As the eyedrops 150 are discharged from the apparatus 140, air pressure within the bottle 146 tends to drop. A pressure equalization tube 180 extends into the bottle 146 to allow entry of additional air as the eyedrops 150 are discharged. As shown, the pressure equalization tube 180 has a hooked portion 181 and has its end 182 positioned at the center of gravity 183 of the volume enclosed by bottle 146 and reservoir 148. Reservoir 148 within housing 142 is of sufficient size so that when a full bottle 146 of eyedrops 150 is inserted in the housing 142 and inverted, the level of eyedrops 150 is below opening 182. Under these circumstances, the opening 182 will be above the eyedrops 150, whatever the orientation of the dispenser. The hooked portion 181 in tube 180 serves to reduce leakage of eyedrops 150 through the pressure equalization tube 180 either through splashing or drainage over the tube 180.

Cylindrical lip 190 on the body 142 is used for positioning the dispensing apparatus 140 in front of the user's eye.

It should now be readily apparent to those skilled in the art that a novel apparatus for the repetitive dispensing of a predetermined quantity of a liquid by application of pressure and cartridge for use in such an apparatus capable of achieving the stated objects of the invention has been provided. Because the apparatus of this invention is of simplified construction, it may be provided in disposable form, already charged with eyedrops 12 or other liquid to be repetitively dispensed in a predetermined quantity. Alternatively, a disposable cartridge containing eyedrops 72 or other liquid to be repetitively dispensed in a predetermined quantity can be inserted into the apparatus. The rotatable, stepped cam mechanism for actuating the apparatus allows the provision of such an appatatus of simplified construction. The pressure relief structure of the invention allows improved operation of a dispensing apparatus of the invention used with a conventional bottle of liquid.

It should further be apparent to those skilled in the art that various changes in form and details of the invention as shown as described may be made. It is intended that such changes be included within the spirit and scope of the claims appended hereto.

What is claimed is:

1. Apparatus for the repetitive dispensing of a predetermined quantity of a liquid comprising a cylinder having a first end and a second end, the liquid to be dispensed within said cylinder, the first end of said cylinder having a restricted opening through which the liquid may pass in response to pressure applied to the liquid, a plunger extending into said cylinder from the second end, a plunger moving member operatively connected to said plunger for moving said plunger in steps toward the first end of said cylinder, an actuating member engaging said plunger moving member by means of opposed surfaces on each said plunger moving and actuating members, one of the opposing surfaces constituting a ramped cam having at least one step and the other of the opposing surfaces having at least one projection engaging the ramped cam opposing surface, and means for biasing said opposed surfaces toward one another, said plunger moving and actuating members being rotatable with respect to each other, the opposing surfaces being configured and positioned so that rotation of said plunger moving and actuating members with respect to each other moves the projection on the ramped cam opposing surface, and movement of the projection over the stop advances said plunger toward the one end a distance corresponding to the step length.

2. The apparatus of claim 1 in which said actuating member is axially disposed around said plunger moving member.

3. The apparatus of claim 1 in which said plunger has a rod extending from the second end of said cylinder and said plunger moving member engages the rod.

4. The apparatus of claim 1 additionally comprising a set of mating threads connecting a rotatable member and a member of said apparatus fixed against rotation, rotation of said plunger moving and actuating members relative to one another also moving the mating threads a longitudinal distance relative to one another corresponding to advancement of the plunger.

5. The apparatus of claim 4 in which said rotatable member and said member fixed against rotation include a keyway and a spline slideably positioned in the keyway.

6. The apparatus of claim 4 in which said rotatable member is said actuating member and said member fixed against rotation is said cylinder.

7. The apparatus of claim 6 in which said cylinder includes a cartridge containing the liquid to be dispensed through the restricted opening, and the restricted opening is formed by a needle mounted in said cylinder to puncture a first end of the cartridge, and said plunger forms a second end of the cartridge.

8. The apparatus of claim 4 in which said biasing means is a spring connected between the end of said plunger moving member opposite from the opposed surfaces and an end of said actuating member opposite from the opposed surfaces.

9. The apparatus of claim 1 in which said cylinder includes a cartridge containing the liquid to be dispensed through the restricted opening, and the restricted opening is formed by a needle mounted in said cylinder to puncture a first end of the cartridge, said plunger forms a second end of the cartridge, and the liquid fills a space between said plunger and the first end of the cartridge.

10. The cartridge of claim 9 in which said actuating member is disposed axially around said biasing member, said actuating and biasing members have removable end caps, and said biasing means is a spring connected between the removable end caps.

11. The apparatus of claim 1 in which the apparatus is for dispensing eyedrops and includes a projecting front member for positioning the restricted opening in front of a user's eye.

12. Apparatus for the repetitive dispensing of a predetermined quantity of a liquid comprising a cylinder having a first end and a closed second end, the first end of said cylinder having a restricted opening through which the liquid may pass in response to pressure applied to the liquid, at least one of the first and second ends being movable within the cylinder toward the other end to change volume of a space defined by the cylinder and containing the liquid, an end moving member operatively connected to the second end for moving the ends in steps toward one another, an actuating member engaging said end moving member by means of opposed surfaces on each said end moving and actuating members, one of the opposing surfaces constituting a ramped cam having at least one step and the other of the opposing surfaces having at least one projection engaging the ramped cam opposing surface, and means for biasing said opposed surfaces toward one another, said end moving and actuating members being rotatable with respect to each other, the opposed surfaces being configured and positioned so that rotation of said end moving and actuating members with respect to each other moves the projection on the ramped cam opposing surface, and movement of the projection over the step advances the ends toward one another a distance corresponding to the step length.

13. The apparatus of claim 12 in which the second end of said cylinder comprises a plunger extending into said cylinder in opposition to the first end and is movable toward the first end.

14. The apparatus of claim 12 in which the second end of said cylinder is fixed and said first end comprises a plug slidably mounted in said cylinder and movable toward the second end.

15. The apparatus of claim 12 additionally comprising a mandrel dimensioned to enter said cylinder as the first end is moved toward the second end, said mandrel including an axially disposed hollow needle for puncturing the first end to form the restricted opening.

* * * * *